United States Patent [19]

Gillonnier et al.

[11] 4,167,522

[45] Sep. 11, 1979

[54] GUANIDINE PANTOATE

[75] Inventors: Claude Gillonnier, Neris-les-Bains; René Moisson, Montlucon, both of France

[73] Assignee: A.E.C. Societe de Chimie Organique et Biologique, Commentry, France

[21] Appl. No.: 939,681

[22] Filed: Sep. 5, 1978

[30] Foreign Application Priority Data

Sep. 5, 1977 [FR] France .................. 77 26823

[51] Int. Cl.$^2$ .......................................... C07C 129/00
[52] U.S. Cl. ........................... 260/501.14; 260/343.6
[58] Field of Search ................................. 260/501.14

[56] References Cited

U.S. PATENT DOCUMENTS

| 3,383,408 | 5/1968 | Lies | 260/501.14 |
| 3,529,022 | 9/1970 | Nakamoto et al. | 562/402 |
| 3,751,454 | 8/1973 | Minami et al. | 260/501.14 |
| 4,028,402 | 6/1977 | Fischer et al. | 260/501.14 |
| 4,080,472 | 3/1978 | Bohuon | 260/501.14 X |

FOREIGN PATENT DOCUMENTS

| 1177856 | 1/1970 | United Kingdom | 562/402 |
| 1395458 | 5/1975 | United Kingdom | 562/402 |

OTHER PUBLICATIONS

Ozegowski et al., Chem. Absts., 55, 390(i), 1961.
Zhdanovich et al., Chem. Absts., 57, 14945(g), 1962.
Fuji, Chem. Absts., 71, 12566(t), 1969.
BASF A.-G., Chem. Absts., 84, 121637(f), 1976.

*Primary Examiner*—James O. Thomas, Jr.
*Assistant Examiner*—G. T. Breitenstein
*Attorney, Agent, or Firm*—Stevens, Davis, Miller & Mosher

[57] ABSTRACT

Guanidine pantoate, which is a new salt of pantoic acid, is of use in the preparation of the optically active isomers of pantolactone and therefrom D-pantothenic acid.

2 Claims, No Drawings

GUANIDINE PANTOATE

The present invention relates to a new salt of pantoic acid (or 2,4-dihydroxy-3,3-dimethylbutanoic acid), viz. guanidine pantoate, in its D and L forms, and mixtures thereof, and also to the use of guanidine DL-pantoate for the preparation of the optically active isomers and their conversion into optically active pantolactone. D-Pantolactone is particularly valuable for the synthesis of D-pantothenic acid which is a constituent of the vitamin B complex.

It is already known to resolve DL-pantolactone by crystallising pantoates of optically active bases. A simpler method, which is known as selective crystallisation or resolution by entrainment (or "by balancing"), consists in alternately crystallising the D and L forms of ammonium or lithium pantoate from a saturated or supersaturated solution of the racemate, in a solvent such as ethanol, which solution has been treated with a suitable proportion of the optical isomer to be separated out (cf. British Pat. No. 1,177,856—Fuji Chemical Industries Limited—and corresponding U.S. Pat. No. 3,529,022, and British Pat. No. 1,395,458—Veb Jenapharm).

The present invention relates to a new salt of pantoic acid, the guanidine salt, which can be used in an advantageous process for the preparation of its optical isomers by entrainment and for the subsequent preparation of optically active pantolactone.

Guanidine pantoate exists in the form of colourless crystals possessing the following characteristics:

Melting point (Kofler bench) DL 152° C., D and L 168° C.; (Mettler oven, in capillary tube) DL 134° C., D and L 154° C.

Optical rotation (for the D and L forms): $[\alpha]_D^{20} = \pm 7.55°$ (c=2, water); $[\alpha]_D^{20} = \pm 22.9°$ (c=2, methanol).

Infra-red spectrum (DL, D and L forms, in paraffin oil)

| 3440–3150 cm$^{-1}$ | 1220 (w) | 980 (m) |
|---|---|---|
| 1660 (s) | 1190 (w) | 910 (m) |
| 1550 (s) | 1155 (w) | 890 (m) |
| 1350 (w) | 1075 (s) | 825 (m) |
| 1310 (m) | 1050 (s) | 755 (s) |
| 1280 (w) | 1025 (w) | 720 (m) | s = strong
m = medium
w = weak

X-ray spectrum

The spectra established from powder diagrams are identical in the case of the D, L and DL forms, the main lines being as follows:

| 5°85 | 10°40 | 12°75 | 15°45 | 18°05 | 20°40 |
|---|---|---|---|---|---|
| 7°52 | 10°50 | 13°05 | 15°85 | 18°40 | 21°20 |
| 7°87 | 11°20 | 13°40 | 16°10 | 19°05 | 21°70 |
| 8°10 | 11°52 | 14°32 | 16°35 | 19°30 | |
| 9°65 | 11°80 | 14°50 | 17°40 | 19°60 | |
| 10°05 | 12°15 | 14°72 | 17°72 | 20°00 | |

Solubility (g per 100 g of solvent)

| | DL | D |
|---|---|---|
| Anhydrous methanol (10° C.) | 31.8 | 13.1 |
| Anhydrous ethanol (10° C.) | 5.4 | 2.3 |
| Ethanol azeotrope (10° C.) | 18.4 | 4.2 |
| Water (5° C.) | 68.8 | 47.5 |

According to a feature of the present invention guanidine pantoate is prepared either by a double decomposition reaction of a metal pantoate with a guanidine salt (for example barium pantoate or calcium pantoate, obtained by the action of the corresponding hydroxide on pantolactone, and guanidine sulphate or carbonate), or directly by the action of guanidine on pantolactone.

Regardless of the variant employed, the reaction is generally carried out in an aqueous medium at a temperature between 0° C. and the reflux temperature of the reaction mixture. If desired, the salt can be isolated either by evaporation of the solution or by precipitation through the addition of a poor solvent such as acetone. According to a still further feature of the invention, an optically active isomer of guanidine pantoate (preferably the D-isomer) is obtained by preparing a saturated or, preferably, supersaturated solution of guanidine DL-pantoate in water or an alcohol containing 1 to 4 carbon atoms, for example methanol or ethanol, or a mixture of such liquids, enriched with the desired optical isomer of the salt, crystallising from the solution the desired optically active isomer of guanidine pantoate, and isolating the crystals of that isomer.

The optically active guanidine pantoate so obtained can then be converted into optically active pantolactone.

Generally, the solution used contains 110 to 135% of the saturation level of guanidine DL-pantoate in the selected solvent at a given temperature, and an amount of the desired optical isomer, for example guanidine D-panotate, which is approximately equal to half the excess amount of guanidine DL-pantoate over the saturation level. The solution is obtained by heating its constituents until all the solid has dissolved. The maximum heating temperature is not critical, provided that it does not cause thermal decomposition of the product.

After cooling and starting the crystallisation by seeding with crystals of the same optical isomer, the desired isomer is collected by filtration when the amount of crystals reaches approximately twice the amount which was initially employed.

An amount of racemate corresponding to the weight of crystalline isomer isolated is then dissolved in the solution, the crystallisation is started by seeding with the other isomer, the crystals of this isomer are collected and so on. Advantageously, a recrystallisation makes it possible to remove the racemate which may contaminate the crystals.

The optically active guanidine pantoate can be converted into optically active pantolactone by known methods, in particular by heating in an acid medium. Guanidine is liberated during the reaction and can be reused.

L-Pantolactone can be racemised after resolution in order to produce a further amount of the D isomer. This operation is described in the literature and does not form part of the invention.

The following non-limitative Examples illustrate the invention.

EXAMPLE 1

Preparation of guanidine DL-pantoate 1580 cc of a 0.478 M aqueous solution of guanidine (0.755 mol) and 104 g (0.755 mol) of 94.4% pure DL-pantolactone are added, under a nitrogen atmosphere, to a round-bottomed flask equipped with a stirrer. After stirring for 5 minutes, the lactone has dissolved and the pH is 11.6. The mixture is heated to 60° C. in the course of 20 minutes and a further 2.45 g (0.018 mol) of lactone are added, the pH then being 9.7. After keeping the temperature at 60° C. for a further 30 minutes, the mixture is concentrated under reduced pressure (10–15 mm Hg) at 50° C. until the total weight is 220 g. 966 cc Of acetone are then added, whilst stirring. After cooling for 2 hours at 5° C. and then for 15 hours at 0° C., the crystals obtained are filtered off and dried at 60° C. under reduced pressure (10–15 mm Hg). 139.3 g Of crude guanidine DL-pantoate, which melts at 129.7° C., are thus obtained.

The mother liquor is evaporated and the residue is then taken up in 9.1 cc of water followed by 173 cc of acetone. A second fraction of 14.45 g of guanidine DL-pantoate, which melts at 126.1° C., is thus recovered.

The D and L isomers are obtained in the following manner.

EXAMPLE 2

Resolution in methanolic solution 43.4 g Of guanidine DL-pantoate and 2.3 g of guanidine D-pantoate are added to a round-bottomed flask which is equipped with a stirrer and contains 100 g of anhydrous methanol. The mixture is heated at 45° C. until all the solid has dissolved, the stirring is then stopped and the mixture is cooled to 10° C. in the course of 20 minutes. 100 mg Of crystalline guanidine-D-pantoate are then added and the mixture is stirred slowly (50 revolutions per minute) for 1 hour at 10° C. The solid is rapidly filtered off, drained and dried in air at 60° C. 4.9 g Of guanidine D-pantoate are obtained.

$[\alpha]_D^{20} = \pm 7.50°$ (c=2, water): optical purity 99.4%

4.9 g Of guanidine DL-pantoate are added to the mother liquor, the mixture is heated at 45° C. until the solid has dissolved, and the preceding operations are repeated, but seeding is carried out with 100 mg of crystalline guanidine L-pantoate. 5.0 g of guanidine L-pantoate are thus obtained.

$[\alpha]_D^{20} = -7.25°$ (c=2, water): optical purity 96%.

EXAMPLE 3

The same procedure as in Example 2 is followed, starting with 613 g of methanol, 261 g of guanidine DL-pantoate and 24 g of guanidine D-pantoate. The volume before seeding (with 0.5 g of crystalline guanidine D-pantoate) is 993 cc.

74 Successive crystallisations are carried out, 46.6 g of quanidine DL-pantoate being added each time and the volume being adjusted to 993 cc with methanol. 1626.7 g of guanidine D-pantoate (optical purity 89%) and 1603.3 g of guanidine L-pantoate (optical purity 92%) are thus obtained.

EXAMPLE 4

Resolution in aqueous solution 748.6 g Of water, 688.8 g of guaniding DL-pantoate and 62.6 g of guanidine D-pantoate, that is to say a total of 1500 g occupying a volume of 1317 cc, are introduced into a 2 liter round-bottomed flask equipped with a stirrer rotating at 160 revolutions per minute. The mixture is heated to 30° C. in the course of 10 minutes and, when all the solid has dissolved, the stirring speed is reduced to 10 revolutions per minute and the mixture is cooled to 5° C. in the course of 20 minutes. Seeding is carried out by adding 0.375 g of guanidine D-pantoate and the mixture is allowed to crystallise at 5° C. for 50 minutes, retaining the same stirring speed. The solid is filtered off and dried in a ventilated oven. 124.9 g of guanidine D-pantoate are thus obtained (productivity: 95 g per liter of solution).

$[\alpha]_D^{20} = +22.5°$ (c=2, methanol): optical purity 97.8%.

125.2 g Of guanidine DL-pantoate are added to the mother liquor and the weight is adjusted to 1500 g by addition of water. The solution contains 689.4 g of guanidine DL-pantoate and 62.3 g of guanidine L-pantoate. The preceding operation is repeated, but seeding is carried out with crystals of guanidine L-pantoate.

The average of 30 complete cycles (that is to say 60 crystallisations), carried out under the same conditions, gave the following results:

| form | weight of DL compound added (g) | weight of isomer isolated (g) |
|---|---|---|
| D | 125.2 | 123.8 |
| L | 125.2 | 123.5 |

| $[\alpha]_D^{20}$ c = 2, methanol) | Optical purity % |
|---|---|
| +22.4° | 97.4 |
| −22.5° | 97.8 |

EXAMPLE 5

Preparation of D-pantolactone 360 g (1.74 mols) of guanidine D-pantoate (obtained as described in Example 3) and 305 cc of 6 N sulphuric acid (0.915 mol) in a 1 liter round-bottomed flask are stirred at 80° C. for 30 minutes and the mixture is then diluted with water to a volume of 700 cc. After extraction with 700 cc of dichloroethane and evaporation of the solvent, 220 g (1.69 moles) of D-pantolactone are obtained.

$[\alpha]_D^{20} = -50°$ (c=1, water).

The aqueous phase contains guanidine in the form of the sulphate which can either be used as so obtained for reaction with calcium DL-pantoate or barium DL-pantoate, or isolated in the form of the free base for reaction with DL-pantolactone.

We claim:

1. Guanidine pantoate in its D and L forms, or mixtures thereof.
2. The compound according to claim 1 which is guanidine D-pantoate.

* * * * *